United States Patent
Nagashima et al.

[11] Patent Number: 5,736,745
[45] Date of Patent: Apr. 7, 1998

[54] CONTAMINATION EVALUATING APPARATUS

[75] Inventors: Makiko Nagashima; Tadashi Nishioka, both of Hyogo, Japan

[73] Assignees: Mitsubishi Denki Kabushiki Kaisha, Tokyo; Ryoden Semiconductor System Engineering Corporation, Hyogo, both of Japan

[21] Appl. No.: 627,655

[22] Filed: Apr. 4, 1996

[30] Foreign Application Priority Data

Jul. 6, 1995 [JP] Japan ................. 7-170909

[51] Int. Cl.$^6$ ................. G01B 11/00
[52] U.S. Cl. ................. 250/559.41; 356/237; 356/375; 250/222.2
[58] Field of Search ................. 250/559.06, 559.29, 250/559.4, 559.41, 559.45, 559.46, 559.48, 222.2; 356/237, 375, 79, 429, 430, 431, 335, 336

[56] References Cited

U.S. PATENT DOCUMENTS

| | | | |
|---|---|---|---|
| 4,659,220 | 4/1987 | Bronte et al. | 356/237 |
| 4,938,654 | 7/1990 | Schram | 414/757 |
| 5,214,282 | 5/1993 | Yamaguchi et al. | 250/307 |
| 5,233,191 | 8/1993 | Noguchi et al. | 250/306 |
| 5,337,140 | 8/1994 | Hagiwara et al. | 356/237 |
| 5,371,375 | 12/1994 | Stern et al. | 250/559.29 |
| 5,422,724 | 6/1995 | Kinney et al. | 356/375 |
| 5,479,252 | 12/1995 | Worster et al. | 356/237 |
| 5,642,298 | 6/1997 | Mallory et al. | 364/561 |
| 5,644,393 | 7/1997 | Nakamura et al. | 356/237 |

FOREIGN PATENT DOCUMENTS

| | | |
|---|---|---|
| 4-305951 | 10/1992 | Japan . |
| 5-21561 | 1/1993 | Japan . |

OTHER PUBLICATIONS

"Dissipation of Contact Electrified Electrons on Dielectric Thin Films with Silicon Substrate" Okusako et al., Jpn. J. Appln. Phys. vol. 33 (1994), pp. L959–L961.

"Limitations on Detecting Particles Sticking to Wafer", Takami et al., Semiconductor World 1994.8, 99.78–83, with English abstract, Aug. 1994.

Primary Examiner—Edward P. Westin
Assistant Examiner—John R. Lee
Attorney, Agent, or Firm—Lowe, Price, LeBlanc & Becker

[57] ABSTRACT

A sample placement portion is fixed to a frame. A stage and a cylindrical piezoelectric element are attached to the sample placement portion, and on this piezoelectric element, a sample (i.e., a semiconductor wafer) is positioned. A light collecting portion and a light receiving portion integrated together are attached slidably to frame for detecting the number and locations of contaminants. In addition, an analyzing portion for analyzing the types of the contaminants is slidably attached to the frame. Accordingly, it is made possible to reduce the size of the apparatus and to perform a highly reliable evaluation of the contamination.

12 Claims, 9 Drawing Sheets

CONTAMINATION EVALUATING APPARATUS

BACKGROUND OF THE INVENTION

1. Field of the Invention

The present invention relates to a contamination evaluating apparatus, and more particularly to a contamination evaluating apparatus for measuring and analyzing the sizes, number and types of contaminants such as small particles sticking on the surface of a semiconductor wafer.

2. Description of the Background Art

Conventionally, a contamination evaluating apparatus which employs Layleigh-Debye approximation or the like for inspecting the sizes and number of contaminants such as small particles on a surface of a semiconductor wafer on the basis of angle distribution of light scattering intensity has been known.

FIG. 11 is a schematic diagram showing a structure of an example of a conventional contamination evaluating apparatus. Referring to FIG. 11, in a conventional contamination evaluating apparatus 700, a sample placement portion 200 having a stage 220 for scanning two-dimensionally a sample (i.e., a semiconductor wafer) 210 is provided. A light projecting portion 100 for generating a light beam 110 irradiated on the surface of sample 210 is also provided. A light collecting portion 300 is placed between light projecting portion 100 and sample placement portion 200 to collect the light scattered by the surface of sample 210. Light collecting portion 300 has a spheroidal shape. At a focus (F2) of the scattered and collected light, a light receiving portion 500 is provided to measure the total amount of the scattered and collected light. In addition, a measurement control portion 600 is provided for driving light projecting portion 100 and sample placement portion 200 while processing an output signal from light receiving portion 500.

Operation of the conventional contamination evaluating apparatus 700 having the above-described structure will now be described. First, a drive signal is transmitted from measurement control portion 600 to light projecting portion 100. As a result, light beam 110 is generated from light projecting portion 100. Light beam 110 passes through a light beam entrance aperture 310 provided at light collecting portion 300 so as to become an incident light 120. Incident light 120 irradiates to a contaminant 230 on the surface of sample 210. The point where incident light 120 and sample 210 cross each other is one focus (F1) of light collecting portion 300. The scattered light generated by the irradiation of incident light 120 to contaminant 230 is collected to the other focus (F2) by light collecting portion 300. The scattered light collected to the focus (F2) is received by light receiving portion 500. Thus, the amount of light scattering intensity corresponding to contaminant 230 is measured. As a result, it is possible to measure the size of contaminant 230. By performing the operation as described above moving along stage 220, it is possible to detect the contaminants 230 on the surface of sample 210 and to measure their sizes and number.

FIG. 12 shows a relationship between the angular distribution of light scattering intensity when there are contaminants 230 on the surface of sample 210 (P) and the angular distribution of light scattering intensity when there are no contaminants 230 on the surface of sample 210 (N).

Referring to FIG. 12, the light scattering intensity obtained when a light scattering angle θ=0 is expressed as $I_0$, and the light scattering intensity obtained at other light scattering angles θ is expressed as I. Normalized $\log(I/I_0)$ is plotted according to the light scattering angle θ. As shown in FIG. 12, the total amount of scattered light is larger when there are contaminants 230 on the surface of sample 210 (P) as compared to the case in which there are no contaminants 230 (N). Accordingly, detection of whether there are contaminants or not, and how many of them if there are any, is made possible. In addition, the sizes of the contaminants 230 can also be known from the amount of light scattering intensity.

However, although it was possible to know whether there are contaminants 230 sticking on the surface of sample 210 and to measure their number and sizes if there are any in the above-described contamination evaluating apparatus 700, there has been a drawback that the types of the contaminants 230 could not be analyzed. If the size of contaminant 230 is large, it is possible to analyze its type by methods such as physical and chemical analyses. However, since miniaturization of the pattern is more and more facilitated in the field of semiconductor devices, contaminant 230 may be 0.1 μm or smaller, making it impossible to apply methods like physical analysis, e.g. Secondary Ion Mass Spectroscopy (SIMS), as described above.

Meanwhile, there are various conventionally suggested methods for analyzing the types of contaminants 230. Japanese Patent Laying-Open No. 5-21561 discloses a technique to provide such apparatus for analyzing the types of contaminants 230 and an apparatus for detecting the number and position coordinates of the contaminants as described above in a single system.

However, in the apparatus disclosed in this Japanese Patent Laying-Open No. 5-21561, the detecting portion for detecting the contaminants and the analyzing portion for analyzing the contaminants are incorporated separately in the system. Therefore, sample 210 must be carried from the detecting portion to the analyzing portion. As a result, the contaminants may move from their original position or it may disappear when the sample is being carried. Also, after the sample 210 is carried from the detecting portion to the analyzing portion, positioning of the sample 210 is done at the analyzing portion. Accordingly, it is highly possible that there may be an error between the location of the origin of position coordinate of contaminant 230 detected at the detecting portion and the location of the origin of position coordinate of contaminant 230 at the analyzing portion. Thus, provision of the detecting portion and the analyzing portion as separate devices has led to a problem that analysis of contaminant 230 after its detection is likely to be inaccurate as well as difficult.

SUMMARY OF THE INVENTION

The present invention was made to solve the problem as described above. It is an object of the present invention to provide a contamination evaluating apparatus in which detection of small contaminants sticking on the surface of a sample and analysis of their types can be performed accurately and easily.

A contamination evaluating apparatus according to the present invention in one aspect includes a guide extending along a horizontal direction, a sample placement portion, a measurement portion, and an analyzing portion. The sample placement portion is fixed to the guide, and a sample is placed thereon. The measurement portion is attached slidably to the guide and is moved onto the sample placement portion so as to measure the number and the locations of the contaminants. The analyzing portion is slidably attached to the guide and is moved onto the sample placement portion so as to analyze the types of the contaminants.

In accordance with a contamination evaluating apparatus of the present invention, in one aspect, a sample placement portion is fixed to a guide. A measurement portion and an analyzing portion move successively along the guide over this fixed sample placement portion so that measurement of the number of contaminants and their locations as well as analysis of their types can be performed. Accordingly, it is not necessary to carry the sample from the measurement portion to the analyzing portion as in the apparatus of Japanese Patent Laying-Open No. 5-21561. Thus, problems such as movement and disappearance of the contaminants or displacement of the sample due to the carrying of the sample can be solved. Accordingly, an accurate and easy evaluation of the contaminants is possible.

A contamination evaluating apparatus in another aspect includes a guide extending along a vertical direction, a sample placement portion, a measurement portion, and an analyzing portion. The sample placement portion is attached slidably to the guide in a vertical direction along the guide, and a sample is placed thereon. The measurement portion is provided above the sample placement portion and measures the number and locations of the contaminants. The analyzing portion is mounted removably on the sample placement portion below the measurement portion and analyzes the types of the contaminants.

In accordance with a contamination evaluating apparatus of the present invention, in another aspect, a sample placement portion is moved in a vertical direction along the guide. A measurement portion is provided above the sample placement portion. Accordingly, number and locations of the contaminants can be measured at the measurement portion by moving the sample placement portion upwards along the guide. When the types of the contaminants are to be analyzed, the sample placement portion is moved downwards along the guide. Then, the analyzing portion is mounted on the sample placement portion so as to analyze the types of the contaminants. As can be understood from the foregoing, the sample is merely moved along the vertical direction while being placed on the sample placement portion within a single apparatus, so that displacement of the sample hardly occurs. In addition, movement and disappearance of the contaminants on the surface of the sample can also be made extremely scarce. Accordingly, evaluation of the contamination can be done accurately and easily.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Embodiments of a contamination evaluating apparatus in accordance with the present invention will be described in the following with reference to FIGS. 1 to 10.

(First Embodiment)

Figure 1:
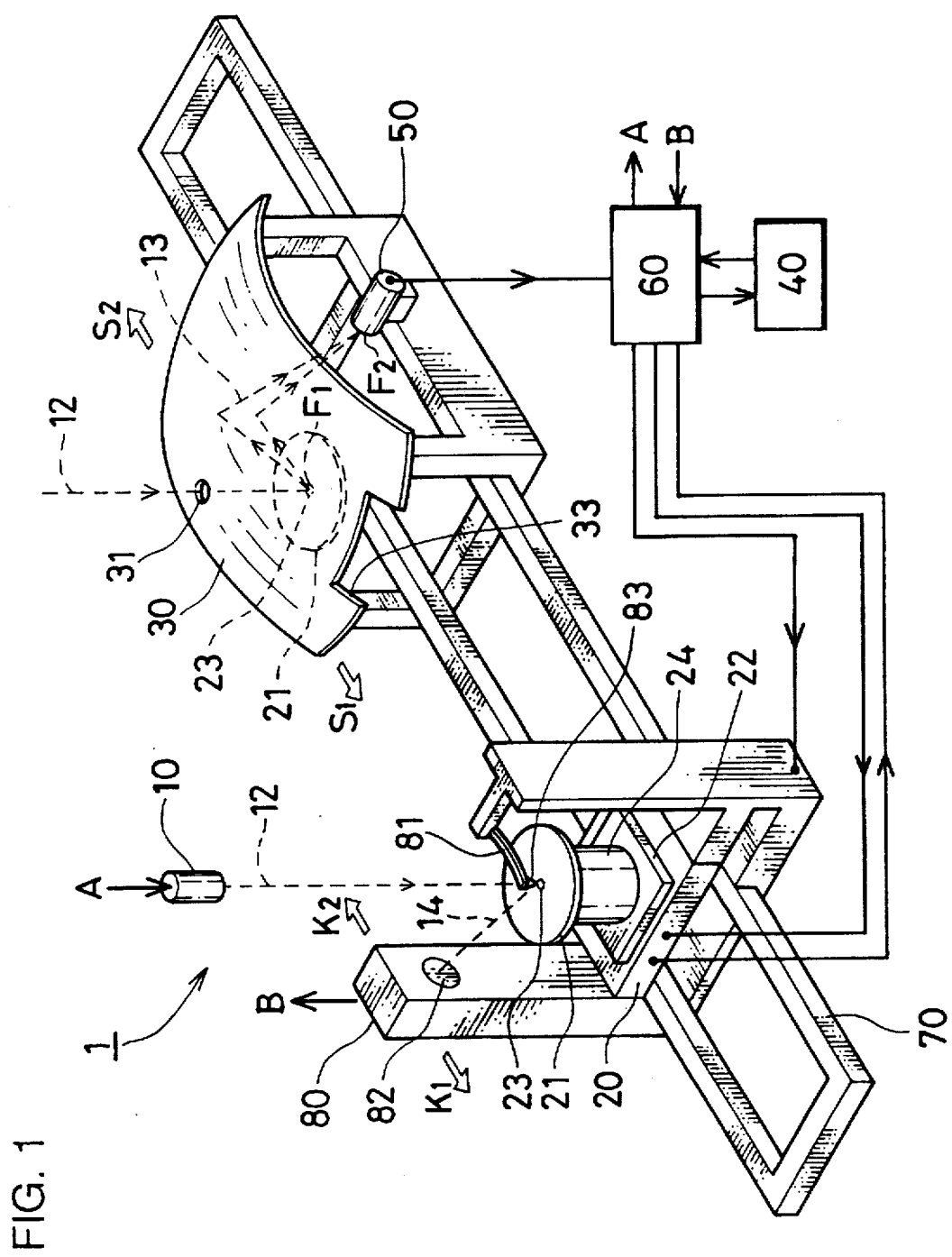
FIG. 1 is a perspective view showing a contamination evaluating apparatus according to a first embodiment of the present invention.

Referring first to FIGS. 1 to 7, a first embodiment according to the present invention will be described. FIG. 1 is a perspective view showing a contamination evaluating apparatus 1 according to the first embodiment of the present invention.

Referring to FIG. 1, contamination evaluating apparatus 1 in the present embodiment includes a light projecting portion 10, a sample placement portion 20, a light collecting portion 30, a memory portion 40, a light receiving portion 50, a measurement control portion 60, a frame 70 which is to be a guide, and an analyzing portion 80.

Light projecting portion 10 is located above sample placement portion 20, and generates a light beam 12 irradiated onto the surface of a sample (i.e., a semiconductor wafer) 21. Sample placement portion 20 is fixed to frame 70 and has a stage 22 for scanning sample 21 two-dimensionally. A cylindrical piezoelectric element 24 exists between sample 21 and stage 22, which element 24 being capable of scanning and moving sample 21 in three-dimensional directions of X, Y, and Z.

Light collecting portion 30 is attached slidably to frame 70. The upper portion of this light collecting portion 30 is formed of a partial spheroid having two focuses F1 and F2. The spheroidal portion of light collecting portion 30 has an inner surface formed of a mirror. In addition, light collecting portion 30 is provided with a light beam entrance aperture 31 through which light beam 12 passes. A notch portion 33 is also provided at light collecting portion 30 for wafer 21 to pass through when light collecting portion 30 is being moved such that the spheroid thereof comes above wafer 21.

A scattered light 13 is reflected by the inner mirror of the spheroid of light collecting portion 30 and is collected at focus F2 where a light receiving portion 50 for measuring the amount of light scattering intensity is located. Measurement control portion 60 is connected to light projecting portion 10, sample placement portion 20, and light receiving portion 50. This measurement control portion 60 controls the operation of light projecting portion 10 and sample placement portion 20 and processes the output signal from light receiving portion 50. More specifically, measurement control portion 60 provides operation control and toning control of light beam 12 as well as feeding operation control of stage 22. In addition, measurement control portion 60 provides operation control of light receiving portion 50 as well as detection of contaminants 23 and calculation of their sizes and number by analyzing the input/output signals of light receiving portion 50. Measurement control portion 60 can indicate the calculated results. Memory portion 40 is connected to measurement control portion 60 to store the information of position coordinates, sizes or number of contaminants 23 at the surface of sample 21.

Frame 70 is of a hollow rectangular shape and has a function of a linear motion guide surface for light collecting portion 30 and analyzing portion 80. Since frame 70 has a shape as described above, its hollow space can be used as a space for drawing out an interconnection. Also, this shape of frame 70 allows weight reduction. Light collecting portion 30 and light receiving portion 50 are integrated and are movable in a sliding manner towards direction S1 or S2. The above-described light collecting portion 30, light receiving portion 50 and measurement control portion 60 form a measurement portion for measuring the number and locations of contaminants 23.

At analyzing portion 80 are provided a cantilever 81 and a light position detector 82 for detecting a displacement of the reflected light 14 of light beam 12 owing to cantilever 81. A probe 83 is provided at the tip of cantilever 81. Analyzing portion 80 and measurement control portion 60 allow an analysis of the types of contaminants 23.

Operation of contamination evaluating apparatus 1 having the above-described structure will now be described. First, analyzing portion 80 shown in FIG. 1 is moved to direction K1. Light collecting portion 30 and light receiving portion 50 are slid towards direction S1 along frame 70 such that light beam 12 from light projecting portion 10 passes through light beam entrance aperture 31. Here, notch portion 33 is provided so that sample 21 is arranged under light collecting portion 30 by passing through it. Then, stage 22 is scanned two-dimensionally in X and Y directions, and when contaminants 23 are detected, the sizes, number and position coordinates thereof are measured by measurement control portion 60. The data obtained are stored in memory portion 40. In this way, detection of contaminants 23 is effected on the entire surface of sample 21.

After this detection of contaminants 23 is completed, light collecting portion 30 and light receiving portion 50 are slid to direction S2, and analyzing portion 80 is slid to direction K2. At this time, positioning of analyzing portion 80 and light projecting portion 10 is performed such that light beam 12 from light projecting portion 10 is irradiated onto cantilever 81.

In addition, a stopper mechanism is provided on frame 70 for positioning light collecting portion 30 and light receiving portion 50 as well as analyzing portion 80 at a prescribed position with respect to stage 22. More particularly, this stopper mechanism provides positioning of light collecting portion 30 and light receiving portion 50 such that light beam 12 is irradiated onto a prescribed location (i.e., the origin of position coordinate) of sample 21 even when light collecting portion 30 and light receiving portion 50 are moved to direction S1. Also, the above-described stopper mechanism allows positioning of analyzing portion 80 such that light beam 12 is irradiated to a position where it is incident on cantilever 81, at a prescribed position (i.e., origin of position coordinate) of sample 21.

Figure 7:
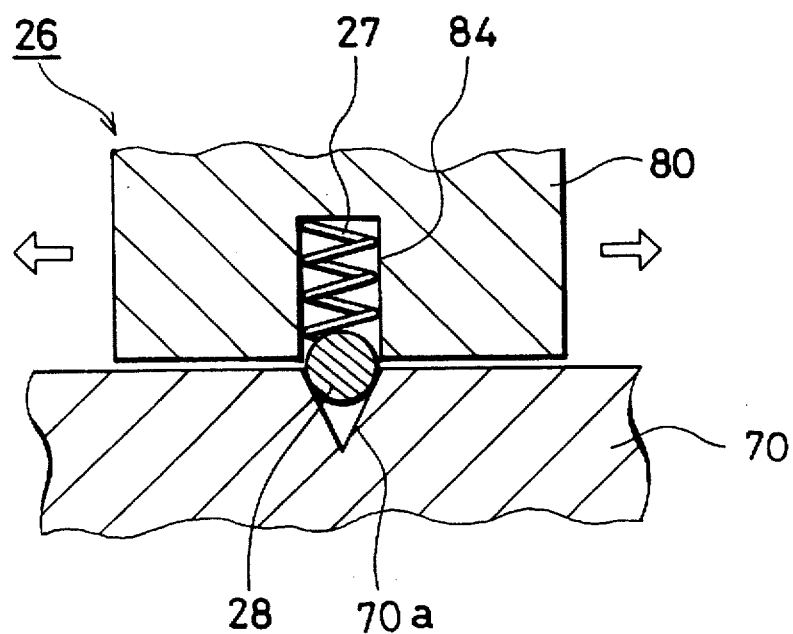
FIG. 7 is a cross sectional view showing a stopper mechanism according to the present invention.

An example of such a stopper mechanism is shown in FIG. 7. FIG. 7 is a cross sectional view of a stopper mechanism 26. Referring to FIG. 7, a V-groove 70a is provided at a prescribed position of frame 70. Meanwhile, a recess 84 is provided at a prescribed position of analyzing portion 80, and within this recess 84, a spring 27 and a ball (metal ball) 28 are located. This ball 28 fits into V-groove 70a so that analyzing portion 80 is positioned at a prescribed location. Light receiving portion 50 is also provided with a stopper mechanism in a similar manner.

Information already stored in memory portion 40 such as location of contaminant 23 is readout by measurement control portion 60. According to this information, stage 22 is driven to move contaminant 23 immediately under conductive probe 83 attached to the tip of cantilever 81. Thereafter, cylindrical piezoelectric element 24 moves sample 21 in a vertical direction (i.e., in direction Z).

Figure 6:
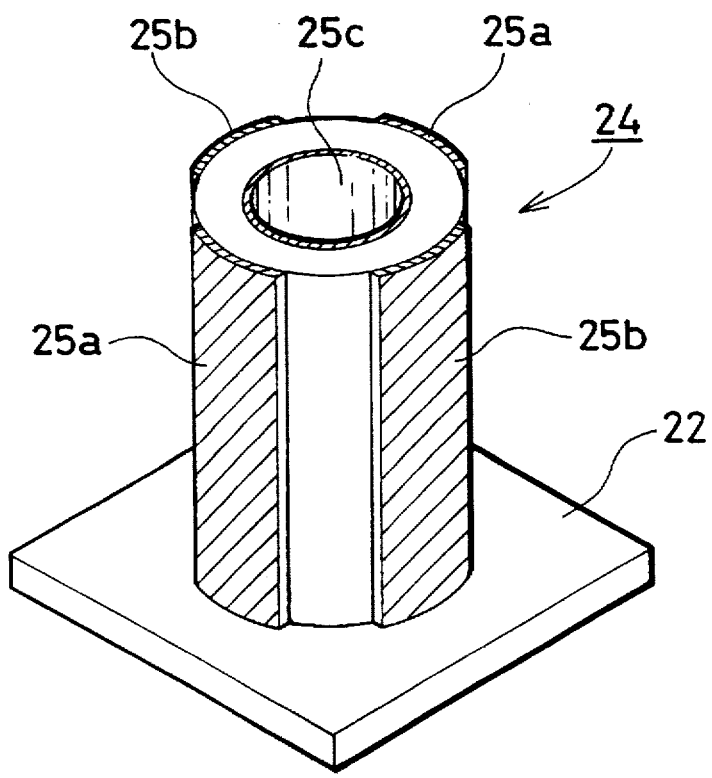
FIG. 6 is a perspective view showing a cylindrical piezoelectric element according to the present invention.

Referring now to FIG. 6, description is made to the structure of cylindrical piezoelectric element 24. FIG. 6 is a perspective view of cylindrical piezoelectric element 24. As shown in FIG. 6, a pair of X-electrodes 25a and a pair of Y-electrodes 25b are formed at locations opposite to one another, respectively, on the outer peripheral surface of cylindrical piezoelectric element 24. This allows expansion along X and Y directions also. In addition, a Z-electrode 25c is formed on the inner surface of cylindrical piezoelectric element 24. By applying a prescribed voltage to Z-electrode 25c, cylindrical piezoelectric element 24 is transformed in a vertical direction (i.e., in direction Z). Thus, sample 21 can be moved upwards so that probe 83 and contaminant 23 comes into contact.

Measurement control portion 60 is provided with a function to apply a DC voltage between conductive cantilever 81 and sample 21. Accordingly, it is possible to apply a DC voltage from this measurement control portion 60 to contaminant 23 to charge this contaminant 23. However, it is necessary to control the flexibility of cantilever 81 before charging contaminant 23 so that this flexibility is maintained constant.

The following is a description of a feedback circuit for controlling the flexibility of cantilever 81 to be constant contact force mode as described above. Provided that cylindrical piezoelectric element 24 has a structure as shown in FIG. 6, a three-dimensional scanning is possible even when stage 22 is stationary. Sample 21 is moved upwards by this cylindrical piezoelectric element 24, light beam 12 is irradiated to cantilever 81, and the reflected light of light beam 12 is received by light position detector 82. Then, an output signal from this light position detector 82 is transmitted to measurement control portion 60. Based on this information, drive voltage of cylindrical piezoelectric element 24 in vertical direction (i.e., direction Z) is controlled by measurement control portion 60 so that flexibility of cantilever 81 is made constant contact force mode. Thus, light position detector 82, Z-electrode 25c of cylindrical piezoelectric element 24 and measurement control portion 60 form a feedback circuit by which it is made possible to control the flexibility of cantilever 81 to be constant. Accordingly, analyzing portion 80 has a function to perform an operation of a well-known Atomic Force Microscope (AFM).

By performing a feedback operation as described above, a three-dimensional scanning operation in X, Y and Z directions by cylindrical piezoelectric element 24 is also possible while controlling flexibility of cantilever 81 to be constant, so as to obtain an atomic force microscope image of contaminant 23. The atomic force microscope image is stereoscopic, and as is well known, allows observation of the shape of contaminant 23 of 0.1 μm or smaller with a high resolution of several tenth of a nanometer, as well as measurement of its size.

After charging contaminant 23 by measurement control portion 60, the contacting operation of probe 83 and contaminant 23 is stopped so as to maintain the distance between them constant. That is, sample 21 is scanned by cylindrical piezoelectric element 24 such that an atomic force microscope image is obtained. As a result, a two-dimensional information of electrostatic force between probe 83 and the charged contaminant 23 can be obtained.

After measurement control portion 60 has applied a constant DC voltage for a certain time period and contaminant 23 has been charged by contact, gradual change in the two-dimensional information for electrostatic force mentioned above is inspected. More specifically, gradual change in the distribution of charge is incorporated as an input data from analyzing portion 80 to measurement control portion 60 which performs processing of that data. Thus, the type of contaminant 23 can be determined. After such evaluation of the contaminant is completed, analyzing portion 80 is slid in direction K1 and sample 21 is taken out.

Referring to FIGS. 2 to 5, principles of operation for determining the type of contaminant 23 by analyzing portion 80 and measurement control portion 60 according to the present embodiment will now be described in detail. FIGS. 2 to 5 are schematic diagrams for illustrating the principles of the operation for determining the type of contaminant 23.

Figure 2:
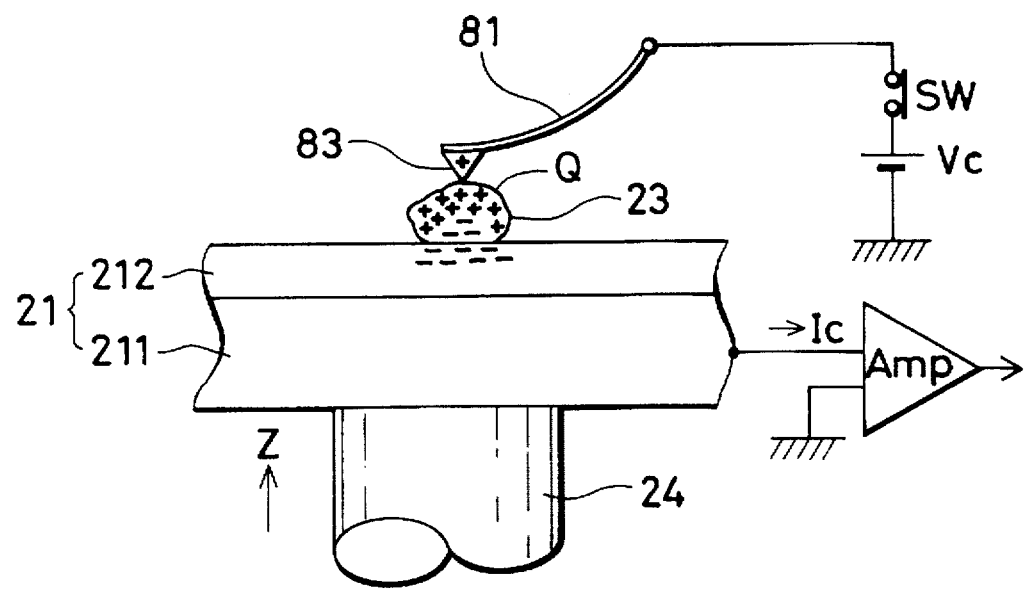
FIGS. 2 and 3 are schematic diagrams illustrating first and second steps in the method of determining the type of a contaminant when it is an insulator.
Figure 3:
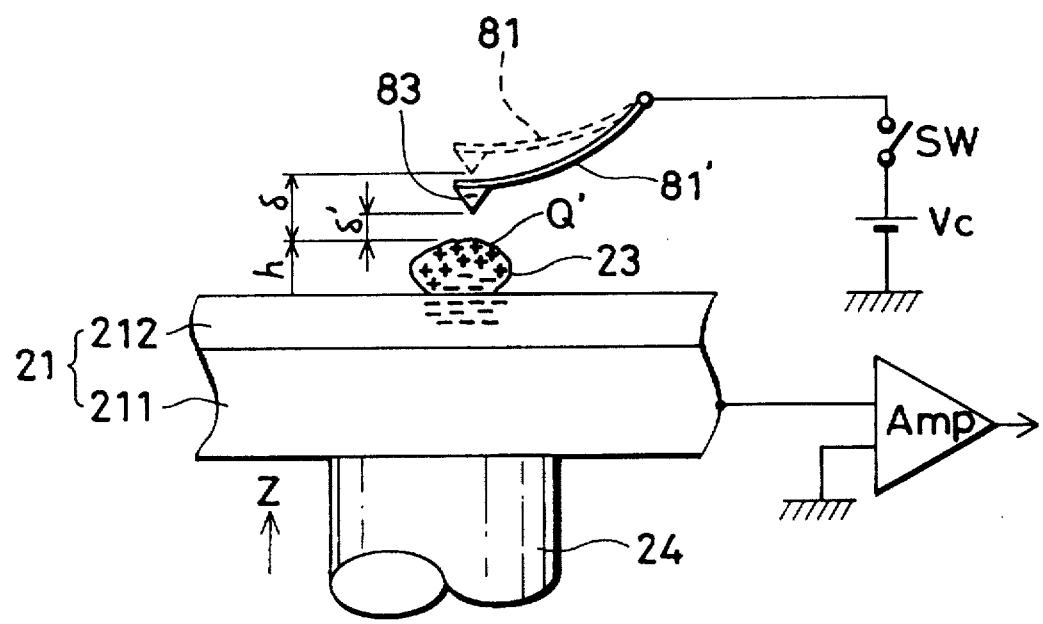

Referring first to FIGS. 2 and 3, description is made to a case in which contaminant 23 is insulative. Referring to FIG. 2, measurement control portion 60 applies a prescribed voltage to Z-electrode 25c of cylindrical piezoelectric element 24 so as to push up sample 21. As a result, contaminant 23 would be in contact with the tip of probe 83. Then, a switch SW is closed, and a DC voltage Vc is applied to contaminant 23 through conductive cantilever 81 and probe 83. Thus, contaminant 23 is charged. The amount of charge at this time is expressed as Q.

In FIG. 2, sample 21 is a semiconductor wafer 21 of, for example, silicon with an insulating film 212 of, e.g., silicon oxide film formed thereon. When contaminant 23 is insulative like an organic substance, charge of an opposite polarity is induced to the lower portion of contaminant 23 and to the surface of insulating film 212. Checking of whether contaminant 23 and the tip of probe 83 is in contact or not is implemented by drawing a so-called Force curve.

Referring next to FIG. 3, switch SW is opened and feedback operation is restarted. Here, as described, contaminant 23 is charged so that charge of an opposite polarity with respect to the charge of contaminant 23 is induced to probe 83. Accordingly, electrostatic force is exerted and probe 83 approaches contaminant 23. Thus, distance δ between probe 83 and contaminant 23 obtained here is shorter as compared to distance δ between probe 83 and contaminant 23 obtained when contaminant 23 is not charged. At the periphery of contaminant 23, distance between probe 83 and insulating film 212 is δ.

Figure 4:
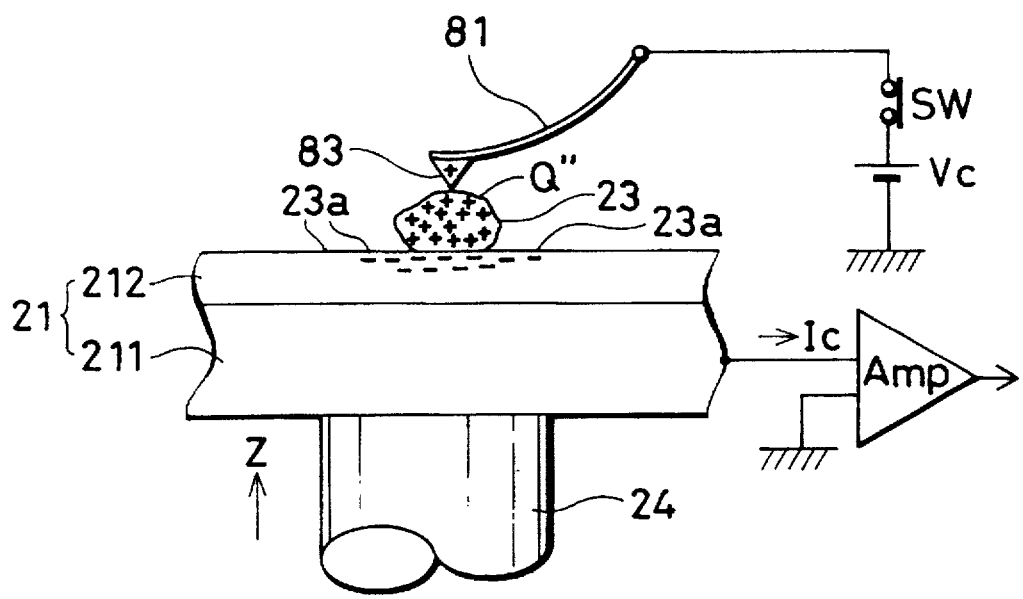
FIGS. 4 and 5 are schematic diagrams illustrating first and second steps in the method of determining the type of the contaminant when it is conductive.
Figure 5:
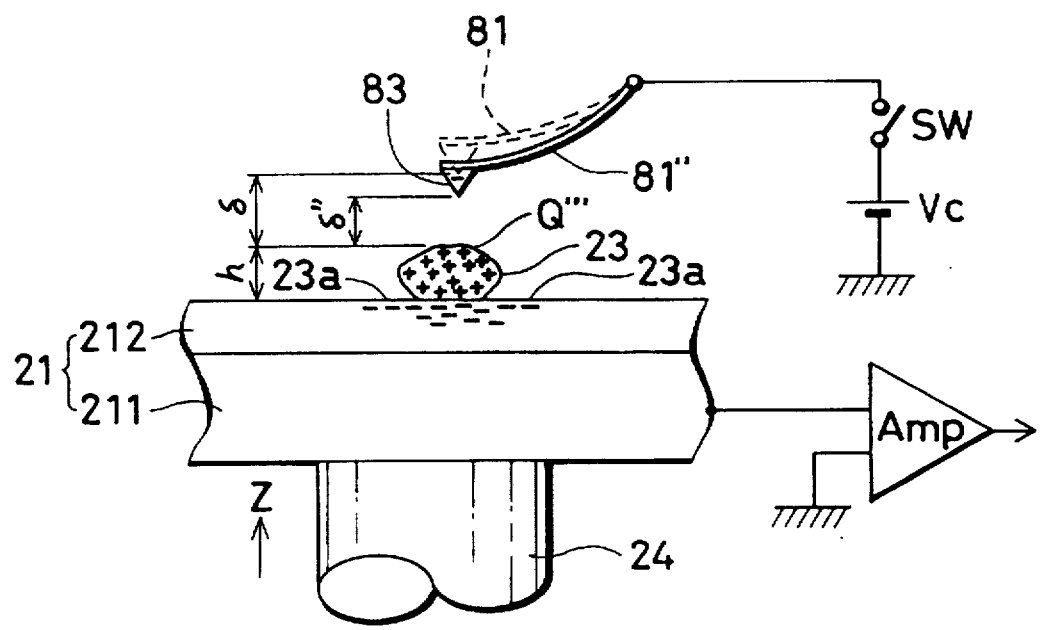

Referring next to FIGS. 4 and 5, description is made to a case in which contaminant 23 is conductive. Referring to FIG. 4, switch SW is closed and voltage Vc is applied to contaminant 23. As a result, the entire contaminant 23 is charged uniformly. The amount of charge at this time is denoted as Q". Then, charge having a polarity opposite to that of the charge constituting the amount of charge Q" is induced to the surface of insulating film 212 located immediately under contaminant 23. In this case, the above-described charge having the opposite polarity is induced not only to portion immediately under contaminant 23 but also to its periphery 23a.

Referring next to FIG. 5, switch SW is opened. Accordingly, charge having a polarity opposite to that of the charge of contaminant 23 is induced to probe 83, and the amount of charge here would be Q". In this case, distance between probe 83 and contaminant 23 is effected by the charge induced at the periphery 23a of contaminant 23 so as to be δ" (where δ">δ').

As has been described above, the electrostatic force is different depending on whether contaminant 23 is conductive or non-conductive, even when the size and shape are the same. When probe 83 is subjected to a three-dimensional fine scanning within a region including contaminant 23 so as to inspect the distribution of electrostatic force, one can know the conductivity of contaminant 23 by checking whether there is an induced charge in the periphery of contaminant 23. In addition, by inspecting the gradual change in the distribution of electrostatic force with switch SW being open, determination of whether it is conductive or non-conductive is possible. With the above principles, types of contaminants 23 can be evaluated by analyzing portion 80 according to the present embodiment as described above.

Based on the foregoing, according to the present embodiment, it is possible to detect the contaminants and to analyze their types without carrying sample 21. Since sample 21 is not carried, displacement of the contaminants hardly occurs. Moreover, light collecting portion 30 or analyzing portion 80 can perform an extremely accurate positioning with respect to sample placement portion 20. Thus, detection of contaminants and analysis of their types can be performed without fail as well as easily, meaning that a highly reliable evaluation of the contamination is possible.

Also, light projecting portion 10 can be shared by light collecting portion 30 and analyzing portion 80. As a result, alignment of optical axis of light projecting portion 10 becomes unnecessary. This also contributes to a highly accurate evaluation of the contaminants. In addition, since light collecting portion 30, light receiving portion 50 and analyzing portion 80 are integrated through frame 70, it is also possible to reduce the size of the apparatus itself.

As a method to determine whether contaminant 23 is conductive or non-conductive, a method described in the following is also applicable. For instance, when sample 21 does not have insulating film 212 on its surface, it is possible to determine whether contaminant 23 is conductive or not by applying voltage Vc as shown in FIG. 2 and examining its relationship with current Ic flowing into sample 21, that is, V-I (voltage-current) characteristics.

In addition, a large voltage Vc may be applied as a pulse to generate corona discharge in a region including contaminant 23 so as to inspect the atomic force microscope image. When contaminant 23 is an organic substance which is likely to be subject to thermal transformation, a significant change appears at the atomic force microscope image around the time of application of voltage Vc. Accordingly, it is possible to determine whether contaminant 23 is an organic substance or not.

Moreover, as shown in FIG. 2, probe 83 is brought into contact with contaminant 23, and a DC voltage is applied thereto. At this time, if current Ic is large, evaluation of contaminant 23 according to tunneling spectrum can be performed. More specifically, when sample 21 does not have insulating film 212 or thickness of insulating film 212 is extremely thin and contaminant 23 is conductive, or when there is no insulating film 212 and non-conductive contaminant 23 having a very small thickness exists, there may be a tunneling current of about 1 nA even if there is a distance of about 1 nm between contaminant 23 and probe 83. In this case, an output of current/voltage (I/V) converter Amp instead of the output of light position detector 82 can be used to cause a feedback operation, such that it serves as a scanning tunneling microscope. Thereafter, feedback operation is temporarily stopped on the position coordinate of contaminant 23 to change voltage Vc. At this state, (dIc/dVc) or (dIc/dVc)/Vc is measured. By performing such tunneling spectrum, it is possible to evaluate the property of contaminant 23 in more detail.

(Second Embodiment)

Figure 8:
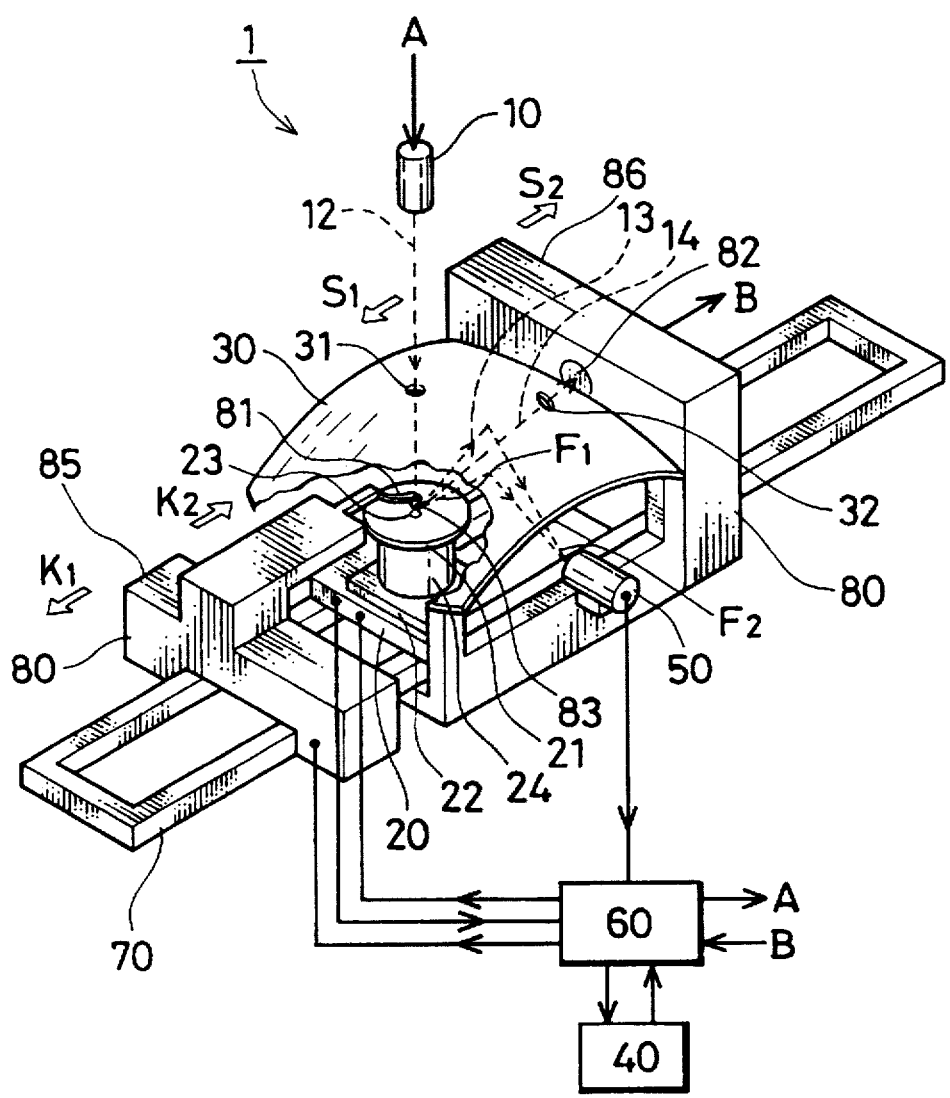
FIG. 8 is a partially cutaway perspective view showing a contamination evaluating apparatus according to a second embodiment of the present invention.

Referring next to FIG. 8, a second embodiment of the present invention will now be described. FIG. 8 is a partially cutaway perspective view showing a contamination evaluating apparatus 1 according to the second embodiment of the present invention.

Referring to FIG. 8, in contamination evaluating apparatus 1, an analyzing portion 80 is divided into a probe lever portion 85 and a reflected light receiving wall portion 86. More particularly, probe lever portion 85 is provided to be laid across a frame 70, and a cantilever 81 extends along the longitudinal direction of frame 70, as shown in FIG. 8. Reflected light receiving portion 86 is provided like a wall along the sides of a light collecting portion 30 and a light receiving portion 50. By having such structure, rigidity of the apparatus can be improved as compared to the first embodiment shown in FIG. 1.

A light position detector 82 is provided at reflected light receiving wall portion 86. In addition to an entrance aperture 31 for a light beam 12, light collecting portion 30 is provided with a reflected light exit aperture 32 to cause incidence of a reflected light 14 of the light irradiated to cantilever 81 such that it reaches light position detector 82. Since other parts of the structure are similar to those of the above-described first embodiment, further description is not given.

(Third Embodiment)

Figure 9:
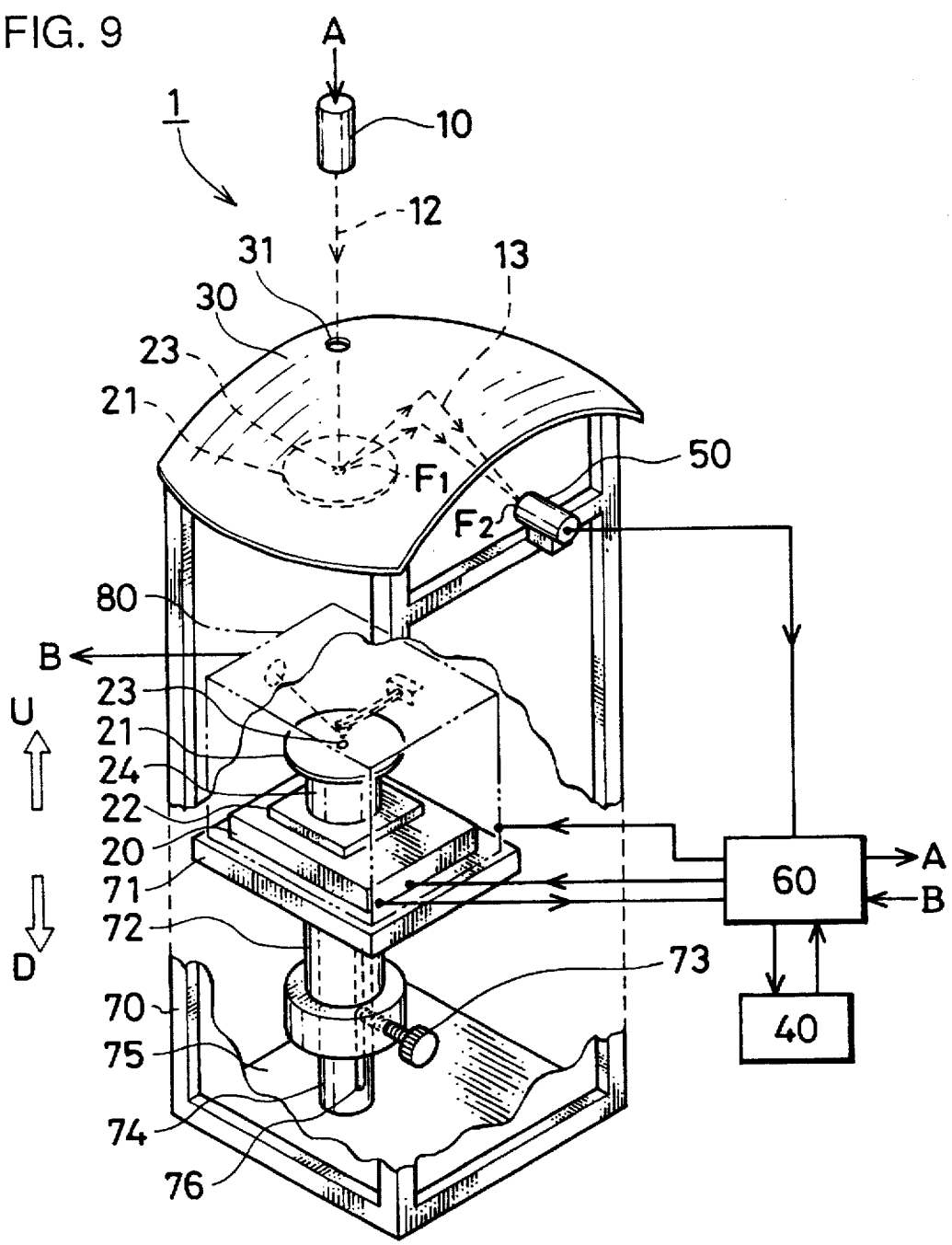
FIG. 9 is a partially cutaway perspective view showing a contamination evaluating apparatus according to a third embodiment of the present invention.

Referring next to FIG. 9, a third embodiment of the present invention will now be described. FIG. 9 is a partially cutaway perspective view showing a contamination evaluating apparatus 1 according to the third embodiment of the present invention.

Referring to FIG. 9, in contamination evaluating apparatus 1 of the present embodiment, a frame 70 has a substantially box-like shape having its inner space, provided with a bottom plate 75 at its bottom portion. A supporting bar 74 is attached to this bottom plate 75, standing perpendicularly to this bottom plate 75. This supporting bar 74 has a function as a guide. A key groove 76 is provided, extending in an axial direction. Supporting bar 74 fits into a sample placement portion fastener 72. A key is inserted to sample placement portion fastener 72, although it is not shown in the figure. This sample placement portion fastener 72 is fixed to a sample placement portion stage 71.

In addition, a fastener set screw 73 is provided at sample placement portion fastener 72. This fastener set screw 73 secures sample placement portion fastener 72 at a prescribed position with respect to supporting bar 74. As described above, fitting supporting bar 74 into sample placement portion fastener 72 allows sample placement portion fastener 72 to slide in a vertical direction along supporting bar 74. Accordingly, sample placement portion stage 71 secured to this sample placement portion fastener 72 is moved in a vertical direction along supporting bar 74. Since a sample placement portion 20 is attached to sample placement portion stage 71, it is moved vertically with this sample placement portion stage 71.

Meanwhile, a light collecting portion 30 is attached to the upper portion of frame 70. Also, to a prescribed position of frame 70, a light receiving portion 50 is attached. In the present embodiment, an analyzing portion 80 has an outer box (shown in phantom line) as can be seen in FIG. 9, which is placed over sample placement portion stage 71 so as to cover sample placement portion 20. Structure of this analyzing portion 80 will be described later in detail.

Operation of contamination evaluating apparatus 1 according to the present invention having a structure as shown in FIG. 9 will now be described. First, sample placement portion 20 is pushed upwards with sample placement portion stage 71 along supporting bar 74 so as to be secured to a prescribed position by fastener set screw 73. Then, detection of whether there are contaminants or not, and of their position coordinates if there are any, is performed in a method similar to that of the first embodiment described previously. Thereafter, this information is stored in a memory portion 40.

Then, fastener set screw 73 is loosened to move sample placement portion stage 71 and sample placement portion 20 downwards. They are secured at a prescribed position by fastener set screw 73. Thereafter, analyzing portion 80 is placed over sample placement portion stage 71. The type of contaminant 23 is determined by a method similar to that of the first embodiment as described previously.

As can be seen from the foregoing, in accordance with the present invention, the number, locations and types of contaminants can be determined just by moving sample placement portion 20 vertically in a single apparatus. Accordingly, disappearance and displacement of contaminants 23 hardly occur. Thus, contaminants 23 can be evaluated accurately and easily. In addition, since only one light projecting portion 10 is required as shown in FIG. 9, alignment of optical axis is unnecessary. Furthermore, by arranging light collecting portion 30 together with light receiving portion 50 and analyzing portion 80 along a vertical direction, it is possible to make the apparatus more compact as compared to the above-described first and second embodiments.

Figure 10:
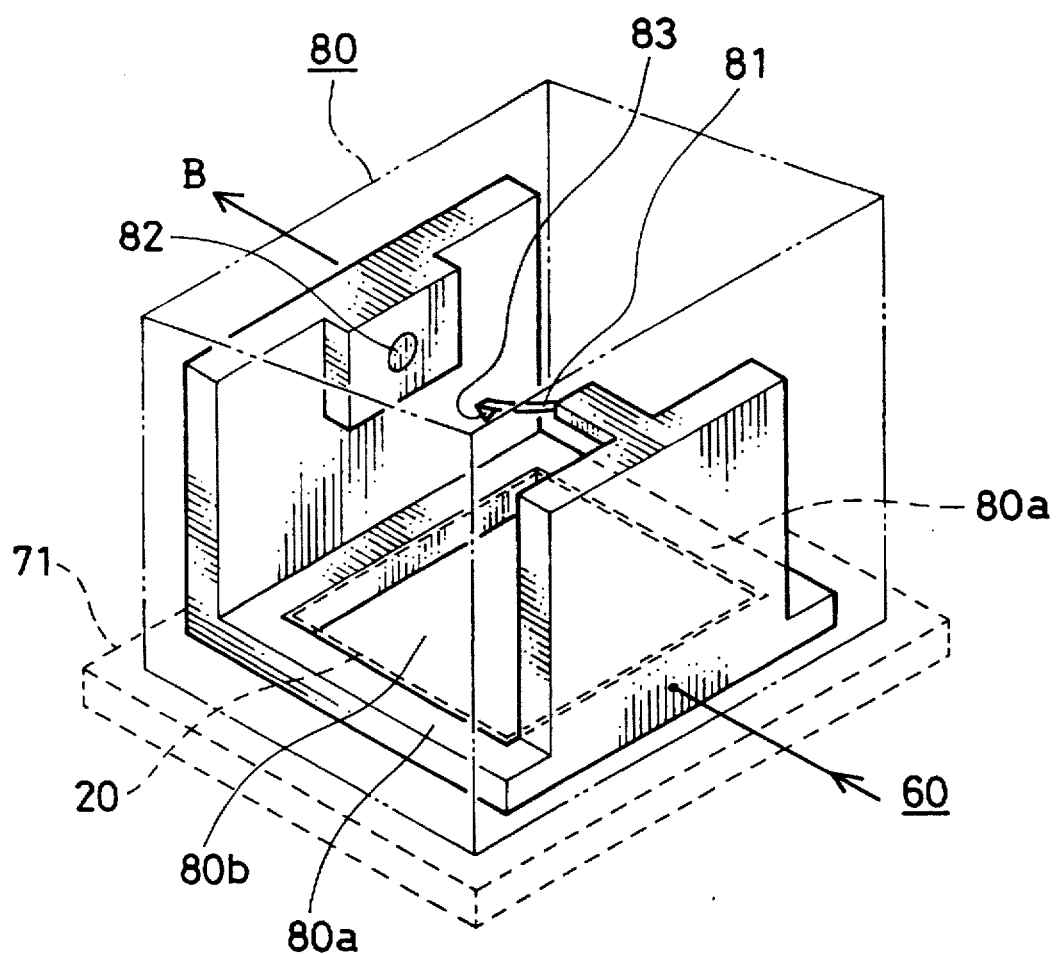
FIG. 10 is a perspective view showing an example of an analyzing portion employed in the third embodiment of the present invention.
Figure 11:
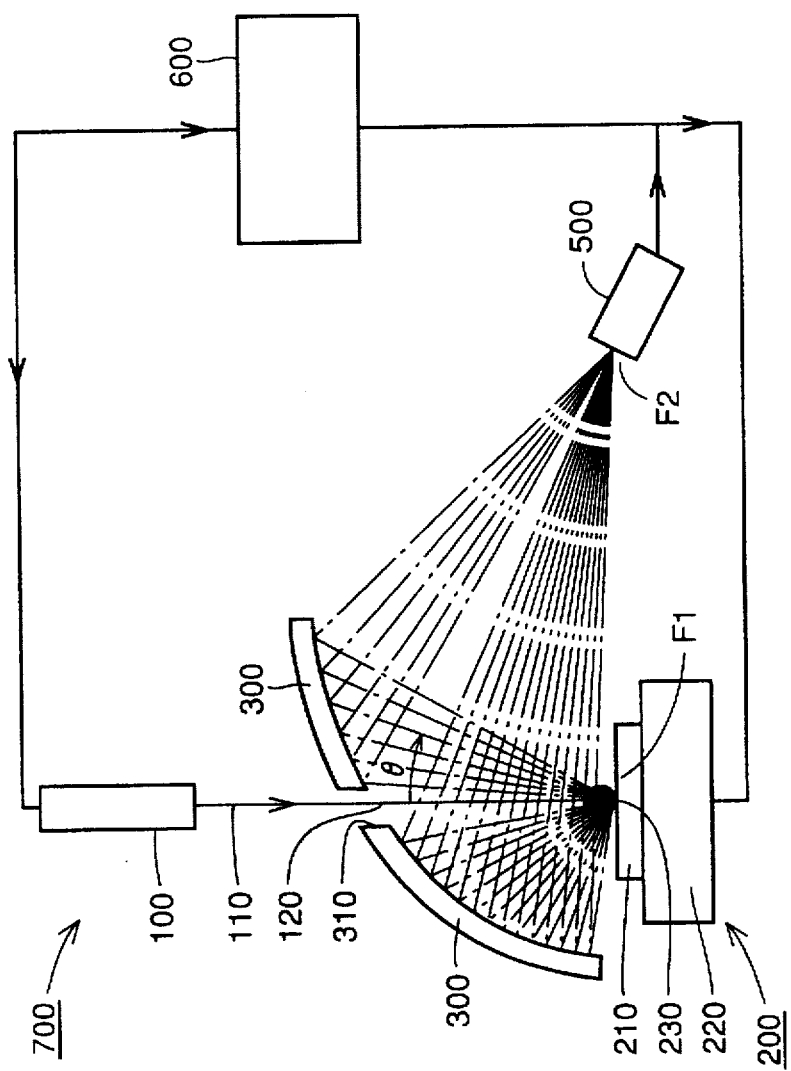
FIG. 11 shows a structure of a conventional contamination evaluating apparatus.
Figure 12:
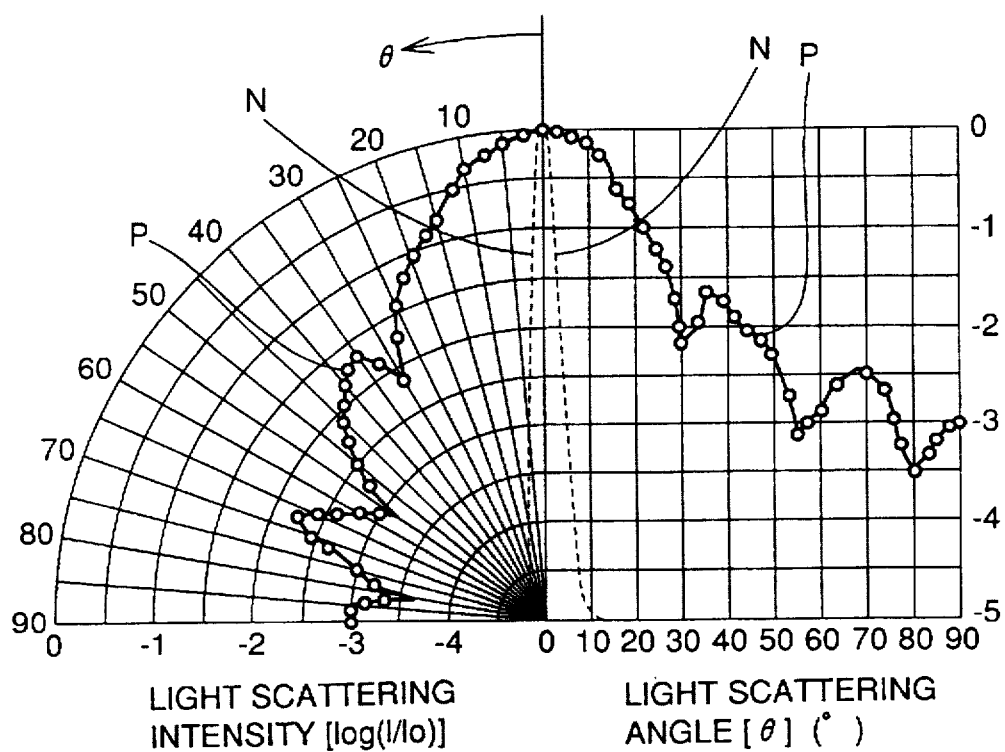
FIG. 12 is a graph showing the relationship between the angular distribution of light scattering intensity when there are contaminants on the surface of a sample (P) and the angular distribution of light scattering intensity when there are no contaminants on the surface of the sample (N).

An example of analyzing portion 80 will now be described with reference to FIG. 10. Referring to FIG. 10, analyzing portion 80 has an outer box made of, for example, metal. With such metal box, external electromagnetic wave can be blocked. In other words, it is made more resistant to noise.

In addition, a pair of standing walls are provided along the inner surface of the opposing side walls of the outer box. The bottom portions of the pair of standing walls are linked by a pair of beams 80a. A light position detector 82 is provided at one standing wall, and the other standing wall is provided with a cantilever 81. By thus providing light position detector 82 and cantilever 81 respectively at the standing walls, relative displacement is suppressed effectively. The above-described pair of standing wall portions and pair of beams 80a define a cavity 80b. The shape of this cavity 80b is similar to that of sample placement portion 20, with a size which is a little larger than the size of sample placement portion 20.

The outer box of analyzing portion 80 is of a shape substantially the same as that of sample placement portion 71, having a size which is a little smaller than sample placement portion stage 71. Accordingly, it is possible to support the bottom surface of the outer box of analyzing portion 80 by the top surface of sample placement portion stage 71 while inserting a stage 22 in cavity 80b. It is preferred that the outer box of analyzing portion 80 is provided with an aperture portion (not shown) for irradiating the light from light projecting portion 10 into analyzing portion 80. With structure as described above, the type of contaminant 23 can be determined in a manner similar to that of above-described first and second embodiments.

Although sample placement portion stage 71 and sample placement portion fastener 72 provided separately have been described in the above present embodiment, they may be integrated. In addition, although it has been assumed that light beam 12 of light projecting portion 10 is used as the light incident on cantilever 81 in the above description, it may also be acceptable to provide a bridge at the upper portion of analyzing portion 80, that is, between the upper side of cantilever 81 and the upper portion of light position detector 82, to provide another light projecting portion at the bridge portion located above probe 83. As the light projecting portion, a semiconductor laser may be used.

In addition, the conductive cantilever can be obtained by coating Cr on the surface of $Si_3N_4$ to a thickness of about 1.5 nm and then additionally coating Au thereon with a thickness of about 50 nm. As the light position detector, a photo-location sensor of a half-split or quarter-split silicon photodiode arrangement can also be employed. As for two-dimensional scanning in X and Y directions of cylindrical piezoelectric element 24, it is possible to drive a computer included in measurement control portion 60 and a D-A converter connected thereto, and to supply voltage to them. Also, when checking the current flowing into cantilever 81 via contaminant 23, an A-D converter is driven, and the current is read by the computer. When a large power supply is needed, and when a small current is read, an amplifier such as an operational amplifier may be provided behind the D-A converter and in front of the A-D converter.

Based on the foregoing, in accordance with the present invention in one aspect, it is made possible to detect the number and locations of the contaminants and to determine their types without carrying the sample. Accordingly, problems such as movement and disappearance of the contaminants which may occur during the time when the sample is carried can be prevented effectively. Thus, a highly reliable evaluation of the contaminants can be performed, and the work itself for evaluation of contaminants is made easier. In addition, by integrating the measurement portion and the analyzing portion to incorporate them in a single apparatus, the apparatus itself can also be reduced in size.

In accordance with a contamination evaluating apparatus in another aspect of the present invention, it is possible to detect the number and locations of the contaminants and to determine their types just by moving the sample in a vertical direction. In this case, since the sample is just moved vertically in a single apparatus, displacement and disappearance of the contaminants hardly occur. Accordingly, a highly reliable evaluation of the contaminants can be performed. In addition, by arranging the measurement portion and the analyzing portion along a vertical direction, it is also possible to reduce the size of the apparatus as compared to the above-described one aspect.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A contamination evaluating apparatus for detecting the number, locations and types of contaminants sticking to the surface of a sample, comprising:
a guide extending in a horizontal direction;
a sample placement portion fixed to said guide and having said sample placed thereon;
a measurement portion attached slidably to said guide for measuring the number and locations of said contaminants by moving onto said sample placement portion; and
an analyzing portion attached slidably to said guide for analyzing the types of said contaminants by moving onto said sample placement portion.

2. The contamination evaluating apparatus according to claim 1, wherein
said measurement portion and said analyzing portion are arranged respectively at opposing sides of said sample placement portion with said sample placement portion therebetween.

3. The contamination evaluating apparatus according to claim 1, further comprising
a single light projecting portion shared by said measurement portion and said analyzing portion, arranged above said sample placement portion, for irradiating light to the surface of said sample placed on said sample placement portion.

4. The contamination evaluating apparatus according to claim 3, wherein
said measurement portion includes:
a light collecting portion having an inner surface formed of a mirror and having a spheroidal shape;
an aperture provided at said light collecting portion for irradiating light generated from said light projecting portion to said sample arranged under said light collecting portion; and
a light receiving portion for receiving a reflected light of the light irradiated to said sample through said aperture,
said analyzing portion includes:
a cantilever having a probe; and
a light position detector for detecting a displacement of a reflected light generated by irradiation of the light from said light projecting portion to said cantilever.

5. The contamination evaluating apparatus according to claim 4, wherein
said light collecting portion is provided with a notch portion for said sample to pass through when said light collecting portion is moved onto said sample placement portion.

6. The contamination evaluating apparatus according to claim 4, wherein
said light receiving portion and said light position detector are connected to a measurement control portion for processing information obtained by said light receiving portion and said light position detector; and
said measurement control portion is connected to a memory portion for storing data processed at said measurement control portion.

7. The contamination evaluating apparatus according to claim 4, wherein
said analyzing portion has a probe lever portion including said cantilever and a reflected light receiving wall portion including said light position detector;
said reflected light receiving wall portion is attached to a side portion of said measurement portion such that said light position detector is located above said light collecting portion;

said light collecting portion is further provided with an aperture for directing a reflected light of the light irradiated to said cantilever to said light position detector;

said probe lever portion is attached to be laid across said guide; and said cantilever extends longitudinally with respect to said guide.

8. The contamination evaluating apparatus according to claim 1, wherein said guide is provided with a stopper mechanism for positioning said measurement portion and said analyzing portion to a prescribed location with respect to said sample placement portion.

9. The contamination evaluating apparatus according to claim 1, wherein said guide is formed of a rectangular frame member having a hollow portion.

10. A contamination evaluating apparatus for detecting the number, locations and types of contaminants sticking to the surface of a sample, comprising:

a guide extending in a vertical direction;

a sample placement portion attached to said guide slidably in a vertical direction along said guide and having said sample placed thereon;

a measurement portion provided above said sample placement portion for measuring the number and locations of said contaminants; and an analyzing portion mounted removably onto said sample placement portion below said measurement portion for analyzing the types of said contaminants.

11. The contamination evaluating apparatus according to claim 10, further comprising a single light projecting portion shared by said measurement portion and said analyzing portion, said measurement portion having a light collecting portion having an inner surface formed of a mirror and having a spheroidal shape;

an aperture provided at said light collecting portion for irradiating light generated from said light projecting portion to said sample arranged under said light collecting portion; and a light receiving portion for receiving reflected light of the light irradiated to said sample through said aperture, said analyzing portion having an outer box arranged to cover said sample placement portion and having an aperture for light generated from said light projecting portion to pass through;

a cantilever attached to said outer box and having a probe; and a light position detector attached to said outer box for detecting displacement of a reflected light of the light generated from said light projecting portion owing to said cantilever.

12. The contamination evaluating apparatus according to claim 11, wherein said outer box is formed of metal;

said cantilever and said light position detector are respectively provided at a pair of standing walls provided along the opposing inner side surfaces of said outer box;

the bottom portions of said pair of standing walls are provided with a pair of beams linking the standing walls; and said sample placement portion is inserted in a space defined by said pair of beams and said pair of standing walls.

* * * * *